US007596469B2

(12) United States Patent
Godara

(10) Patent No.: US 7,596,469 B2
(45) Date of Patent: Sep. 29, 2009

(54) METHOD AND APPARATUS FOR PRIORITIZING ERRORS IN A MEDICAL TREATMENT SYSTEM

(75) Inventor: Neil Godara, Mississauga (CA)

(73) Assignee: Baylis Medical Company Inc., Montreal (CA)

( * ) Notice: Subject to any disclaimer, the term of this patent is extended or adjusted under 35 U.S.C. 154(b) by 0 days.

(21) Appl. No.: 11/470,835

(22) Filed: Sep. 7, 2006

(65) Prior Publication Data

US 2007/0027653 A1 Feb. 1, 2007

Related U.S. Application Data

(63) Continuation-in-part of application No. 11/425,868, filed on Jun. 22, 2006, now Pat. No. 7,533,002, which is a continuation of application No. 10/893,274, filed on Jul. 19, 2004, now Pat. No. 7,076,399.

(51) Int. Cl.
*G06F 15/00* (2006.01)

(52) U.S. Cl. ....................... 702/183; 702/185; 600/300; 607/17; 340/573.1

(58) Field of Classification Search ................. 702/183, 702/185; 600/300, 508, 544, 547, 595, 587; 607/8, 17, 89, 67, 68, 48; 340/573.1
See application file for complete search history.

(56) References Cited

U.S. PATENT DOCUMENTS 4,058,001 A 11/1977 Waxman
4,124,894 A 11/1978 Vick et al.
4,881,230 A 11/1989 Clark et al.
5,133,020 A * 7/1992 Giger et al. ................. 382/128
5,429,123 A 7/1995 Shaffer et al.
5,600,574 A 2/1997 Reitan
5,891,179 A 4/1999 Er et al.
5,914,875 A 6/1999 Monta et al.
6,421,554 B1 7/2002 Lee et al.
6,438,408 B1 8/2002 Mulligan et al.
6,565,562 B1 5/2003 Shah et al.
6,788,965 B2 9/2004 Ruchti et al.
6,975,968 B2 * 12/2005 Nakamitsu et al. .......... 702/184
7,127,376 B2 * 10/2006 Nashner ..................... 702/185
2002/0115939 A1 8/2002 Mulligan et al.
2003/0060692 A1 3/2003 Ruchti et al.
2003/0074029 A1 4/2003 Deno et al.
2003/0195774 A1 10/2003 Abbo
2004/0039605 A1 * 2/2004 Bardy ........................... 705/2
2004/0133119 A1 * 7/2004 Osorio et al. ............... 600/544
2004/0147969 A1 * 7/2004 Mann et al. ................... 607/17
2004/0167580 A1 * 8/2004 Mann et al. ................... 607/17
2004/0193068 A1 * 9/2004 Burton et al. ............... 600/544
2005/0027323 A1 2/2005 Mulligan et al.
2005/0042681 A1 * 2/2005 Van Eyk et al. .............. 435/7.1
2005/0203497 A1 * 9/2005 Speeg et al. .................... 606/15
2005/0215914 A1 * 9/2005 Bornzin et al. .............. 600/508
2005/0278001 A1 * 12/2005 Qin et al. ...................... 607/48
2006/0009810 A1 * 1/2006 Mann et al. ................... 607/17

(Continued)

OTHER PUBLICATIONS

Notice of Allowance for 1145-35, "Mailed on Feb. 14, 2006".

(Continued)

*Primary Examiner*—Carol S Tsai
(74) *Attorney, Agent, or Firm*—Dimock Stratton LLP

(57) ABSTRACT

A method and apparatus are disclosed for detecting, analyzing and displaying errors in a medical treatment system. Detected errors are analyzed to define further errors. Errors may be classified, for example, in response to severity, and prioritized. Prioritization may depend on a scope of the error, an order of occurrence, importance, or other factors.

23 Claims, 2 Drawing Sheets

U.S. PATENT DOCUMENTS

2006/0059145 A1 * 3/2006 Henschke et al. .............. 707/6

OTHER PUBLICATIONS

Ex Parte Quayle Action for 1145-35, "Mailed on Nov. 4, 2005".
Final Action for 1145-47, "Mailed on Jun. 2, 2008".
Non Final Action for 1145-47, "Mailed on Jan. 2, 2008".
Non Final Action for 1145-47, "Mailed on May 7, 2007".
Notice of Allowance in US Patent Application 11/425,868, mailed on Dec. 31, 2008.

* cited by examiner

METHOD AND APPARATUS FOR PRIORITIZING ERRORS IN A MEDICAL TREATMENT SYSTEM

REFERENCES TO PARENT AND CO-PENDING APPLICATIONS

This application claims priority from and is a continuation-in-part of U.S. patent application Ser. No. 11/425,868, filed Jun. 22, 2006 now U.S. Pat. No. 7,533,002, which is a continuation of U.S. patent application Ser. No. 10/893,274, filed Jul. 19, 2004, now U.S. Pat. No. 7,076,399 issued on Jul. 11, 2006.

TECHNICAL FIELD

The invention relates to medical generators, for example, for electrosurgical applications, and more particularly to controls for such generators.

BACKGROUND OF THE ART

Medical generators are widely used in medical treatment systems. Their numerous functions include: supplying energy for treatment, communicating with measuring, monitoring, and/or treatment devices, controlling the activity of one or more peripheral treatment devices (such as pumps or suction devices), computing and analyzing input data, and displaying or otherwise communicating treatment information to a user. With such a wide range of uses, medical generators often communicate with multiple devices, each of whose operational parameters may depend on the activity of other devices.

The complexity of multiple inputs and interactions, which gives medical generators their versatility and utility, can also cause more opportunities for errors to arise. These errors can often be difficult for a user to diagnose because of the multiple possible causes of a single problem. For example, in a medical treatment system that monitors impedance while energy is delivered to a tissue through a probe, an excessively high impedance measurement could be caused by vaporization of the tissue, a malfunctioning impedance monitor, or a disconnection of the treatment device.

It is often necessary to identify the causes of errors and to fix the errors as quickly as possible to ensure safety, due to the delicate nature of some medical treatment procedures. Frequently, however, individuals operating a medical treatment system do not have a technical background or a detailed knowledge of the way the system works. If there is an error in the operation of the medical treatment system, these users may not understand how to solve the error and may not recognize whether an error is signaling a more fundamental problem. Compounding this complexity are differences in component function with different modes of operation, meaning that one error may have different causes at different times.

Currently, some medical generators for use in medical treatment systems use a coded display requiring a user to look up an error code in documentation which may raise follow-up questions to help troubleshoot the problem further. This approach can be time consuming and inconvenient during a medical procedure. Some medical generators use an on-screen display that informs the operator of an error and may suggest possible courses of action. However, many errors, such as high impedance, may have a variety of possible causes and suggested courses of action for resolution. In these cases, it can be time consuming to determine which course of action will resolve the error. If multiple errors are detected additional time and effort will be required to determine whether the errors are jointly or independently caused, and which course(s) of action will optimally and efficiently resolve all errors.

U.S. Pat. No. 6,788,965, issued Sep. 7, 2004 to Ruchti et al, discloses a system for detecting errors and determining failure modes related to a non-invasive blood glucose monitor. Ruchti et al. disclose an error detection system that employs a hierarchical series of levels to determine whether or not a given glucose measurement is invalid. Each level utilizes different criteria (e.g. rudimentary specifications, patient history, etc.) for determining the validity of the measurement. Ruchti et al. do not describe a medical treatment apparatus with various functions, modes of operation or multiple inputs/outputs and do not describe an error logic system that may solve the difficulties associated with such an apparatus as described above.

A solution which addresses one or more of these shortcomings is desired.

SUMMARY OF THE DISCLOSURE

In one broad aspect, embodiments of the present invention comprise a method of prioritizing errors in a medical treatment system comprising a energy source and at least one associated device, the method comprising: detecting at least two errors in the operation of at least one of the energy source and the at least one associated device; and prioritizing at least one of the at least two errors based on at least one characteristic of each of the at least two errors.

BRIEF DESCRIPTION OF THE DRAWINGS

In order that the invention may be readily understood, embodiments of the invention are illustrated by way of examples in the accompanying drawings, in which.

DETAILED DESCRIPTION

Figure 1:
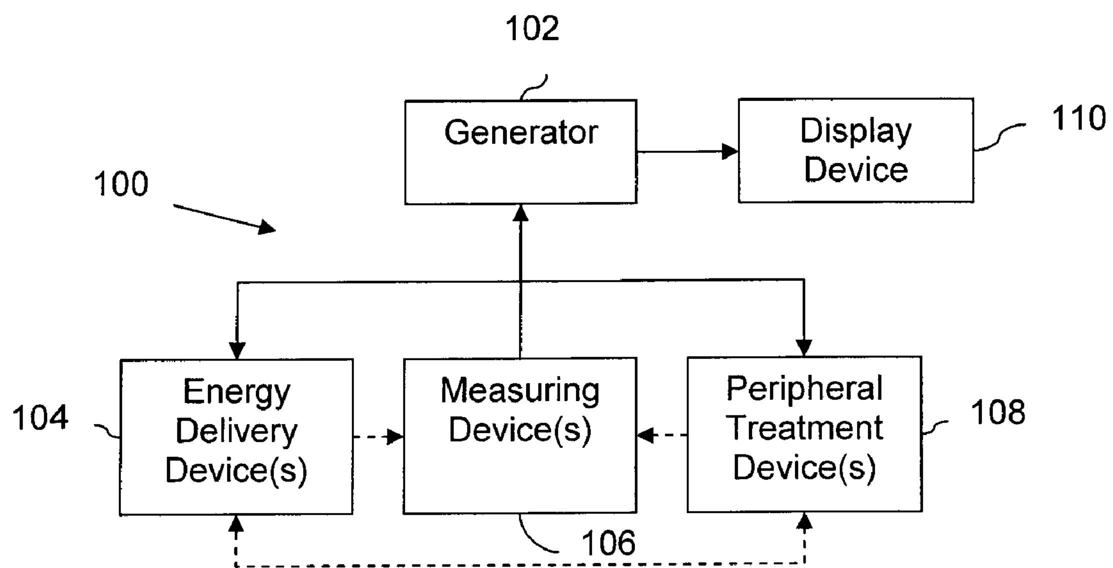
FIG. 1 illustrates a block diagram of an exemplary medical treatment system in which the present invention can be used.

A first embodiment of the invention provides a method of error detection and analysis to be used in an energy source, for example a generator 102, that supplies energy to a system 100 used to treat pain in an animal body, particularly a human (FIG. 1). The system 100 comprises a generator 102 for delivering energy through one or more energy delivery devices 104. Generator 102 may also control the activity of one or more peripheral treatment devices 108, such as pumps. Generator 102 can have many inputs, including measuring devices 106 (such as temperature and impedance monitors), inputs that relay information on the presence or type of attached devices (104 or 108) for example by using an integrated circuit. Attached devices 104 and 108 may be unconnected to one another, may communicate among each other or be connected to one another (for example, an energy-delivering probe having an internal channel to carry cooling fluid from a pump), and/or may be physically connected to the measuring device(s) 106 (for example, an energy delivering probe having a thermocouple mounted in the tip).

Figure 2:
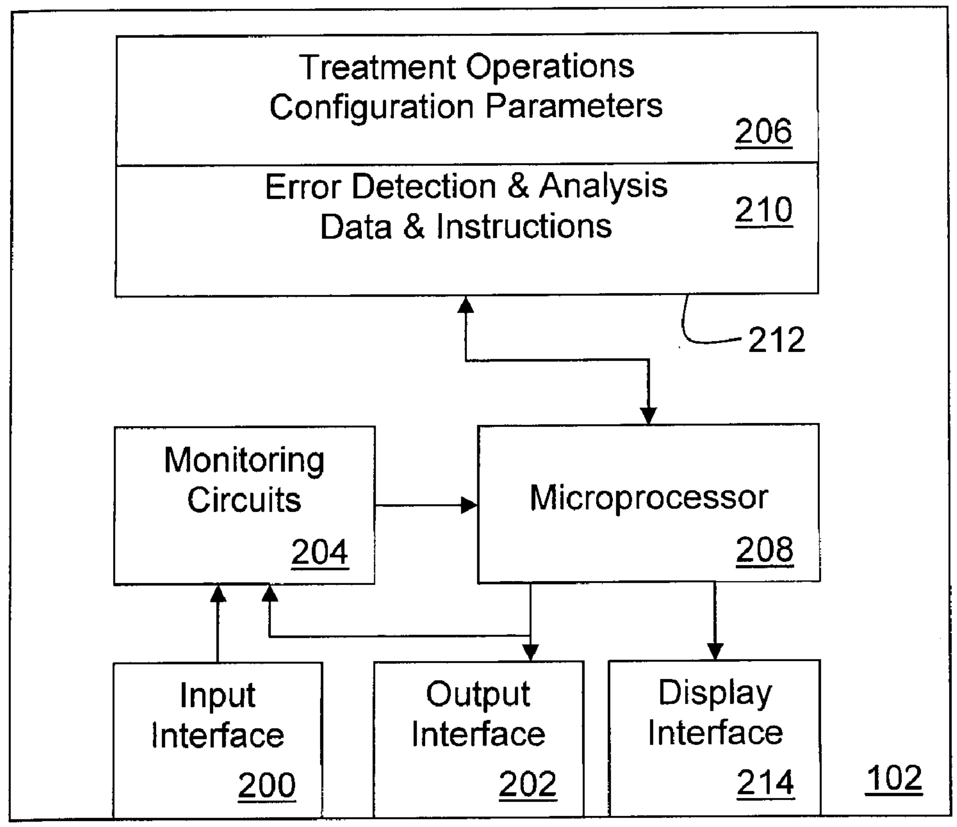
FIG. 2 illustrates a block diagram of the components of a generator in accordance with one embodiment of the invention.

FIG. 2 shows an illustrative embodiment of the components of generator 102. Generator 102 comprises an input interface 200 for receiving inputs from measuring devices 106 and, as applicable, attached devices 104 and 108. An output interface 202 supplies output for controlling or communicating with attached devices 104 and 108 and, as applicable, measurement devices 106. Monitoring circuits 204 monitor input received via input interface 200 (i.e. input measurements) and monitor output for supply via output interface 202 (i.e. output measurements). Information from the monitoring circuits 204 is communicated to an error detecting unit, such as a microprocessor 208, configurable by data and instructions 210 for error detection and analysis which may be stored in a memory 212. Configuration parameters 206 stored in memory 212 can also provide input to the microprocessor 208. Generator 102 further includes a display interface 214 for outputting a display of error information as further described below. Though shown as separate input and output interfaces, persons of skill in the art will appreciate that a combined input/output interface (I/O) may be employed. Though not shown, input interface 200, output interface 202 or an additional input, output or I/O interface may be coupled to one or more user input devices (keyboard, microphone, pointing device, scanner, etc.), storage devices, or communication networks for inputting, outputting or communicating data and commands for the operation of the generator, whether treatment operations or error detecting and analysis operations. While shown locally coupled to generator 102, memory 212 may be remotely located and coupled for communication with generator 102 via a suitable interface (not shown). Display interface 214 may couple generator 102 to a display device 110 (e.g. a monitor) or may comprise a communications interface to another system such as a computer system having a display device for receiving output of the display of the errors.

In some embodiments, generator 102 may further comprise an event data recorder, which may be associated with, for example, microprocessor 208 and/or memory 212. The event data recorder may be operable to store data associated with the operation of generator 102 and/or any devices associated with generator 102 such that the data may be retrievable in the event that generator 102 were to fail. Data that may be stored by the event data recorder includes, but is not limited to, any errors detected in the operation of generator 102 and/or any devices associated with generator 102, input measurements, output measurements, control signals, configuration parameters and/or treatment parameters. In the event of failure of generator 102, data regarding the operation of generator 102 prior to failure may be retrieved from the event data recorder for analysis, thus facilitating diagnosis of the cause of failure of generator 102.

Figure 3:
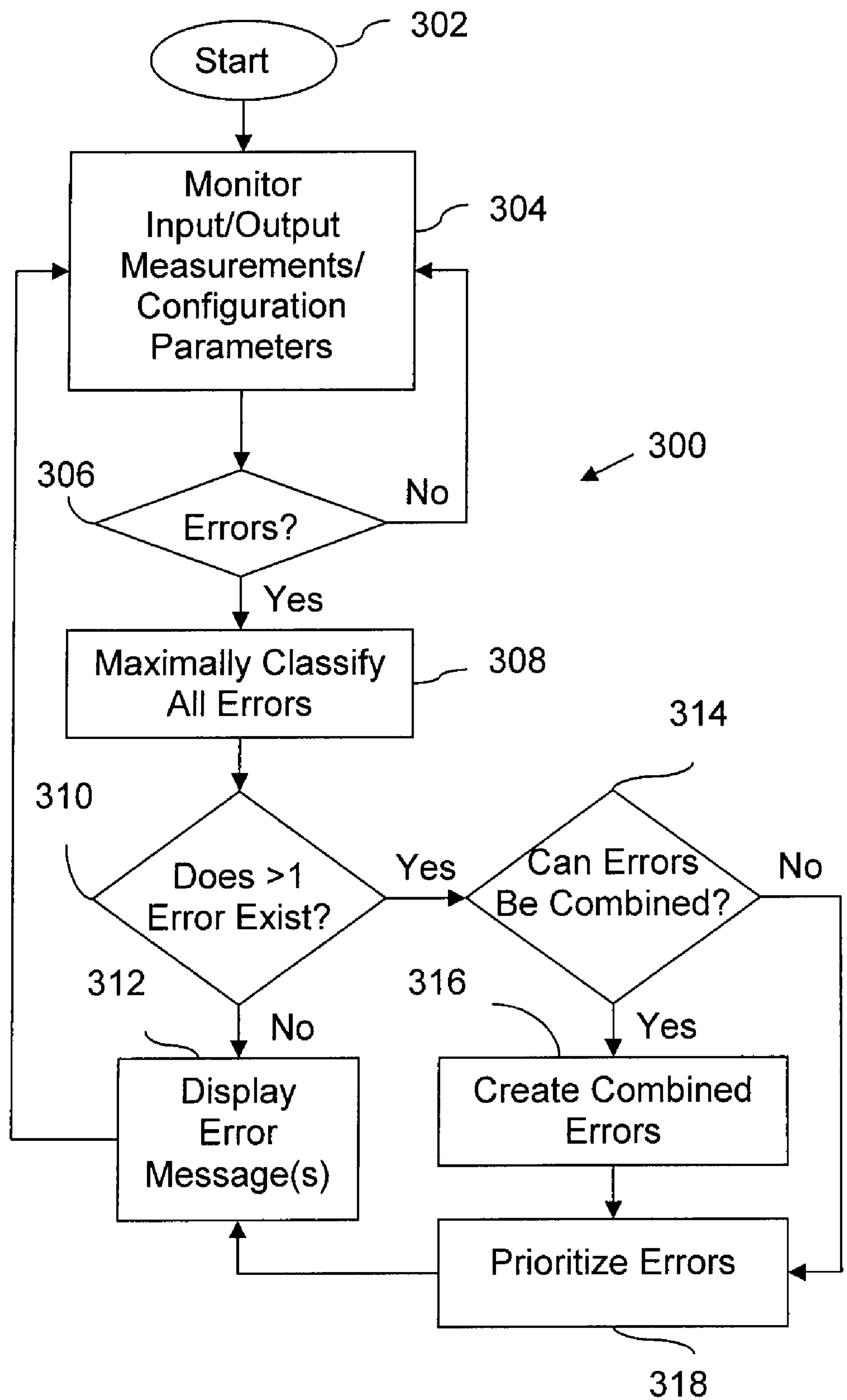
FIG. 3 illustrates a flow chart of operations for performing hierarchical error logic in accordance with an aspect of the invention.

FIG. 3 is a flowchart of operations 300 for error detection and analysis, according to a method aspect of the invention. In accordance with the preferred embodiment, operations 300 begin at start block 302, for example, following assembly of system 100 and power up. At step 304, input and output measurements are continuously monitored and measured values are compared to respective predefined threshold values or ranges of allowed values, on an ongoing basis. If a measurement is within a threshold or range, no error is generated at step 306 (No branch). When a measurement is beyond a threshold or outside a range, an error is generated (step 306, Yes branch). Errors can also be generated by comparing current system settings, or configuration parameters 206, to predefined values; for example, if it has been predefined that the system 100 must reach a set temperature and the total time for the treatment has been predefined, then an error will be generated if the preset time for the system 100 to reach the set temperature (ramp time) is greater than the total preset time for the treatment.

Multiple input and output measurements may be monitored allowing the generation of multiple errors at step 306 via Yes branch to step 308. Once an error is generated, operations 300 classify the error in response to specific conditions of the error. For example, if an invalid temperature measurement is detected, operations 300 may classify the temperature measurement as too low or too high. Many levels of increased specificity of classification may occur. For example, for a temperature measurement that is classified as too low: if the temperature measurement is between 5° C. and 15° C., the error classification may indicate a properly functioning device but a temperature too low to operate; if the temperature measurement is below 5° C., the error classification may indicate a malfunctioning temperature sensor. At step 308 errors will be classified to the maximum extent. An embodiment of a method of classification is discussed further herein below.

If at step 310 it is determined that only a single error exists, a detailed error message is displayed describing the error at step 312. Preferably, corrective action that can be taken to resolve the error is suggested. In one alternate embodiment (not shown), the display of errors (step 312) is coincident with or precedes an automated modification of the operations of generator 102, such as the halting of energy delivery or switching to another mode based on the errors generated.

At step 310, if it is determined that multiple errors exist, operations 300 proceed via Yes branch to step 314. At this point, the set of errors is analyzed in order to determine whether any errors can be combined, being symptomatic of a particular problem. For example, simultaneous errors showing high impedance and an invalid temperature measurement may be indicative of a broken connector or disconnected device. In a preferred embodiment, the first detected errors are combined to form second errors, if applicable. The combination may be determined with reference to a predetermined lookup table or logic tree, discussed further below, which lists all possible first errors and the ways in which at least some of those first errors may be combined to form new (i.e. second) errors. If at least some of these first errors can be combined (step 314, Yes branch), such first errors are combined to form second errors (step 316). Any remaining uncombined first errors remain as independent errors (step 314, No branch). All second (i.e. combined) errors and remaining first (i.e. independent) errors are preferably prioritized (step 318).

At step 312, first and second errors can be displayed one at a time, or can be displayed in a number of other ways including simultaneously, with all errors appearing at once, in groups, or on separate screens that can be toggled or scrolled. For example, the errors may be displayed in stacked and/or staggered windows, wherein a higher priority error may be displayed in the foreground, for example at least partially obscuring at least one lower priority error. In such embodiments, resolving the higher priority error may cause the display of the higher priority error to be cleared, in effect unobstructing the display of the next highest priority error.

In the preferred embodiment, prioritization of first and second errors 318 is responsive to the degree of complexity of resolving each error, or degree to which resolving one error will resolve other concomitant errors. For example, an error that requires an entire treatment device to be changed is prioritized over an error that requires repositioning a device and not changing the device. As a further example, trend analysis may be used to help determine a likely root cause of an error, as described in more detail below. In such a case, the error detected by the trend analysis may be given a high priority due to the fact that a likely root cause has been determined, such that resolving this error may help to resolve one or more other errors. However, prioritization of errors may also be based on a number of other factors including, but not limited to, the severity of the error, the measurable parameter to which the error relates, the magnitude of the measured parameter that led to the error (for example, the amount of voltage overshoot or measured temperature), the order in which the error was detected, or any other characteristic by which errors can be sorted. For example, in some embodiments, errors may be prioritized based on the relative severity of each error rather than the absolute magnitude of the errors. In other words, if two separate errors are detected, each related to a different parameter of energy delivery, the errors may not be prioritized based on the absolute magnitude of the measured parameters, since the parameters differ, but may rather be prioritized based on the relative severity of each error. For example, an error based on a temperature overshoot of 15 degrees may have a lower priority than a voltage overshoot of 10 V, even though the absolute magnitude of the temperature error is higher than the voltage error, since the voltage error may be indicative of a more severe system failure. Prioritization of errors may occur following the classification of errors, for example as Type 1, 2 or 3 errors as described herein below.

Grouping and prioritizing errors may aid a user in resolving system problems quickly and with minimal confusion, which can help ensure patient safety by reducing treatment disruption as both error diagnosis and correction times are minimized. For example, as may occur with a prior art device, a user may receive two concurrent errors showing high impedance and invalid temperature measurement with no indication of what is causing the errors. In such a case, the user would have to check all possible sources of each error, to determine the actual cause(s) of the errors, and to determine whether each error was caused by a problem with the equipment or by a potentially dangerous problem with the treatment itself (e.g. high impedance being caused by tissue vaporization). Knowing if the actual cause of both errors is simply that a device has become disconnected, will allow the user to quickly resolve the problem and continue with the treatment, in accordance with a goal of the present invention.

In some embodiments of the present invention, the generator itself may facilitate troubleshooting or diagnosis of one or more detected errors. For example, a generator may be operable to perform one or more test procedures to test the integrity, stability or performance, for example, of an internal generator component or an external device associated with the generator. In some such embodiments, a generator may deliver one or more electrical signals, for example test voltages or current signals, to an associated device in order to ascertain whether or not the device has failed and, if so, where the point of failure may have occurred. For example, a generator may employ Time-Domain Reflectrometry (TDR) analysis to determine the point of wire damage in a cable/probe combination, in order to ascertain whether the point of failure lies in the probe or in the cable. In other words, if a user receives a high-impedance error, it may be indicative of a damaged electrical conductor between the generator and the probe. In order to further diagnose the error, the generator may deliver a test signal to the probe via the cable connecting the probe to the generator and may detect a return signal from the probe/cable combination. If a return signal is detected, this may be indicative of a break in the conductive pathway between the generator and the probe, leading to a reflection of the signal back to the generator. The generator may then employ TDR in order to determine how far along the conductive pathway the failure has occurred, in order to ascertain whether the failure is in the cable, probe or, alternatively, in the generator itself. In some embodiments, a system of the present invention may further comprise one or more components to allow one or more associated devices to be connected to the generator, for example in a loop-through connection, in order to enable the generator to test those devices, as described above.

In further embodiments, one or more of the associated devices may be operable to transmit one or more signals to the generator to indicate a mode or point of failure of the device. In such embodiments, the generator may not necessarily be able to perform the testing procedures described above but may be operable to receive signals indicative of device failure from the associated devices and analyze those signals in order to more accurately determine the root cause of a detected error.

While FIG. 3 shows a general flowchart of operations for analyzing and clarifying errors, the criteria by which errors are defined can vary in a number of ways. In the preferred embodiment, the sets or ranges of acceptable output or input measurements, or the thresholds above or below which errors are triggered, such as ranges of temperature, can be changed, or may be made dependent on the values of other measured parameters. As well, in the preferred embodiment, a mode of operation or progress through a treatment procedure, can affect the classification of errors.

In one embodiment, three different types of errors (e.g. type 1, type 2 and type 3) may be produced depending on the mode of operation or procedural progress. The operation of the generator 102 may be responsive to the type of error produced. Type 1 errors are generated when immediate patient and/or equipment protection is required. For a type 1 error, treatment operations of the system 100 may be automatically modified, discontinuing all generator output to energy delivery devices 104 and/or peripheral treatment devices 108. Further treatment using the system 100 requires a system reset. Type 1 errors cannot be immediately resolved by the user and have the highest priority.

Unlike a type 1 error, type 2 errors are anticipated to be correctable by the user and treatment may progress once they have been resolved. Generator 102 may respond to a type 2 error by modifying the operation of the system 100 either discontinuing all generator output 202 to energy delivery devices 104 and/or peripheral treatment devices 108 or switching the operation of the system 100 to a predetermined mode of operation dependent on the error. The errors remain displayed until the problem(s) that cause them is (are) resolved.

Type 3 errors have the lowest priority of the three types of errors; treatment operations of the system 100 need not be automatically halted or suspended by generator 102 and clear after being briefly displayed, or upon being cleared manually by the user. Whether a given error is classified as a type 1, 2, or 3 error depends on the current mode of operation. For example, an invalid impedance measurement in a standby mode may be due to a reasonable action by the user, such as a removal of a probe in order to inject additional treatment fluid through the introducer needle, but the same invalid impedance measurement in an energy delivery mode could indicate vaporization of body tissue or faulty equipment.

Another factor that can affect the classification of errors is the configuration parameters 206 within generator 102. In the preferred embodiment, generator 102 can be configured to expect a certain number or type of device(s) to be connected to it, and can generate errors based on this expectation. For example, if generator 102 is configured to apply radiofrequency energy through one probe, and two probes are connected, an error will be displayed in order to inform the user of excess connections, even if the probe through which energy will be delivered is working correctly.

While the embodiment discussed above describes a system 100 capable of analyzing errors as they occur, based on predetermined criteria, it is also possible that such a system 100 could include analysis of trends in measurements in order to detect errors (for example, producing an error if the temperature drops about 10° C. in about 1 second, wherein the error is detected based on a change in temperature over time, rather than only producing an error if the temperature apparently instantaneously drops below a certain level, wherein the error is detected based on a specific temperature value), or that such a system 100 could detect errors based on analysis of trends in errors (for example, repeated high impedance errors in a given mode, occurring with greater frequency than could be attributed to user actions, can indicate a frayed wire). Trends may be analyzed over the course of one or more treatment procedures or over the course of an extended period of time, for example one or more days or weeks or any other period of time. For example, intermittent connectivity during RF delivery, if occurring with a variety of probes, cables and grounding pads, for example over the course of a single procedure or several procedures over a period of time, may be attributable to a faulty conductive pathway (for example a wire or electrical conductor) within the generator itself. Trend analysis can also be used to create type 3 errors, or warnings of imminent errors. For example, if repeated high temperature errors were to be generated, a type 3 error could be produced to warn the user that they are in danger of causing permanent damage to the system 100 (type 1 error imminent). In one embodiment, ranges of acceptable input data for error determination are dependent on trend analysis of errors; for example, if repeated errors are generated based on a certain measurable parameter, the sensitivity of measurement of that parameter could be automatically adjusted (increased or decreased). Trend analysis may be based, for example, on one or more of: frequency, classification and magnitude of the detected errors and/or measurements.

Table 1 shows a portion of a logic tree as used in one embodiment for the classification of errors in a lesion-making system 100. In this example, the lesion-making system 100 comprises a generator 102, up to two probes 104 each furnished with electrodes (i.e. one active electrode and one return electrode) for the delivery of energy, measuring devices including a thermocouple and an impedance monitor 106, and may comprise a grounding pad to be used to the receive the delivered energy. In the example of Table 1, the system 100 is configured to deliver energy through only one probe 104, and is in "READY" mode, prior to the delivery of energy.

TABLE 1

| LESIONING (READY) (Secondary Probe disabled) | | |
|---|---|---|
| | CHECK 1 Primary Probe Thermocouple temperature valid? | |
| Result | Pass | Fail |
| Action | Goto CHECK 3 | Goto CHECK 2 |
| | CHECK 2 Valid Impedance between RF Active and RF Return? | |
| Result | Pass | Fail |
| Action | E01 | E02 |
| | CHECK 3 Secondary Probe Thermocouple temperature not present? | |
| Result | Pass | Fail |
| Action | Goto CHECK 4 | W11 |
| | CHECK 4 Valid Impedance between RF Active and RF Return? | |
| Result | Pass | Fail |
| Action | Goto LESIONING ON - INITIALIZATION (Secondary Probe disabled) | If High: W12 If Low: W13 |

Consider, as an example, a system configured according to Table 1, whereby a thermocouple 106 mounted on probe 104 was not functioning. In this example, CHECK 1 would find the Primary Probe Thermocouple temperature to be invalid and fail, moving to CHECK 2. If the impedance measurement was valid, CHECK 2 would pass and error E01 would be displayed informing the user of a temperature error. Table 2 lists a portion of the display messages for system 100 of the present embodiment. If, in a contrasting example, the probe 104 was properly connected, but was not in contact with the tissue, CHECK 1 would find the Primary Probe Thermocouple temperature to be valid and pass to CHECK 3. CHECK 3 would find no indication of the presence of a second probe 104 and pass to CHECK 4. CHECK 4 would find an invalid impedance between the two probes 104 and fail, creating an error. The invalid impedance error would further be classified as a high impedance error, causing error W12 (see Table 2) to be displayed. If, in the system 100 used in the above examples, a probe 104 were disconnected, both invalid temperature and high impedance errors would result. In this example, CHECK 1 would find the Primary Probe Thermocouple temperature to be invalid and proceed to CHECK 2. CHECK 2 would then find the impedance to be invalid and would fail, displaying error E02, as described in Table 2, which informs the user that the probe 104 is not connected. Thus, rather than displaying separate errors for invalid temperature and high impedance, the invention produces a third, unique, combined error.

TABLE 2

| Type | Code | Displayed Message |
|---|---|---|
| TYPE 2 | E01 | Invalid Temperature Reading Check Probe and Cable Connections Possible defective probe or cable. Try new probe and cable if problem persists |
| TYPE 2 | E02 | Probe Not Connected Check probe and cable connections. Probe or cable(s) may be defective |
| TYPE 2 | E03 | Temperature Out-of-range Outside 15-100° C. expected range. Probe or cable may be defective |
| TYPE 2 | E04 | Secondary Probe Connected But Disabled in Advance Settings Disconnect Secondary Probe or, if desired, enable Secondary Probe in ADVANCED SETTINGS |
| TYPE 2 | E05 | High Impedance Detected Check Probe and Cable Connections. Probe or Cable may be defective |
| TYPE 2 | E06 | Low Impedance Detected Check probe and cable connections. Possible short circuit in probe or cable |
| TYPE 3 | W11 | Secondary Probe Connected But Disabled in Advance Settings Disconnect Secondary Probe or, if desired, enable Secondary Probe in ADVANCED SETTINGS |
| TYPE 3 | W12 | High Impedance Detected Check Probe and Cable Connections. Probe or Cable may be defective |

TABLE 2-continued

| Type | Code | Displayed Message |
|---|---|---|
| TYPE 3 | W13 | Low Impedance Detected<br>Check probe and cable connections. Possible short circuit in probe or cable |

Table 3 provides a manner to classify errors for a system 100 configured to deliver energy through only one probe 104, similar to Table 1, which is in "ON" (energy delivery) mode. As described above, a system 100 may be configured to have different thresholds above or below which errors are detected, depending on operating modes, or could classify errors differently depending on a current operating mode. For example, in a system 100 configured according to Table 3, if a probe 104 is properly connected but is not in contact with the tissue while energy is delivered, CHECK 1 would find the Primary Probe Thermocouple temperature to be valid and pass to CHECK 3. CHECK 3 would find no valid measurement to indicate the presence of a second probe 104 and pass to CHECK 4. CHECK 4 would find an invalid impedance and fail, creating an error. The invalid impedance error would further be classified as a high impedance error, causing error E05, as shown in Table 2, to be displayed. Unlike error W12 in the above example, which corresponds to a Type 3 error, and would display on the generator screen for a number of seconds, but would not modify the treatment operations of the system 100, error E05 is a Type 2 error and generator 102 will respond to modify its operations to halt treatment operations (i.e. discontinuing the delivery of energy). Thus, the type of error can depend on a mode of operation of the generator.

TABLE 3

| LESIONING ON (Secondary Probe disabled) | | |
|---|---|---|
| CHECK 1 Primary Probe Thermocouple temperature valid? | | |
| Result | Pass | Fail |
| Action | Goto CHECK 3 | Goto CHECK 2 |
| CHECK 2 Valid Impedance between RF Active and RF Return? | | |
| Result | Pass | Fail |
| Action | E03 | E02 |
| CHECK 3 Secondary Probe Thermocouple temperature not present? | | |
| Result | Pass | Fail |
| Action | Goto CHECK 4 | E04 |
| CHECK 4 Valid Impedance between RF Active and RF Return? | | |
| Result | Pass | Fail |
| Action | Goto LESIONING DONE (Secondary Probe disabled) | If High: E05<br>If Low: E06 |

Tables 1 and 3 show a portion of logical configuration data for detecting and analysing errors based on a physical configuration of the system 100. For example, if a system 100 were configured to deliver energy through only one probe 104, as in Table 1, but had 2 probes 104 connected, the system 100 would find the Primary Probe Thermocouple temperature to be valid and pass to CHECK 3. CHECK 3 would then detect the presence of a valid temperature reading from the thermocouple 106 attached to the second probe 104 and would fail, displaying error W11, which instructs the user to either remove the second probe 104, if it is not intended to be used, or to enable the use of the second probe 104 (Table 2).

Variations to the embodiments and examples described above include, but are not limited to: types of inputs or outputs, the language or classification (e.g. a numbering system) used in the display of error messages, the manner of communicating errors (including displaying the messages, or communicating the errors to other devices for displaying and/or other use), the criteria for combining errors, the classification of types or degrees of error, and/or the specific physical configuration of a medical treatment system using such an error logic, may be employed by any user that is skilled in the art, and are intended to be included within the scope of the invention. The scope of the invention is therefore intended to be limited solely by the scope of the appended claims.

I claim:

1. A method of prioritizing errors in a medical treatment system comprising an energy source and at least one associated device, the method comprising:

detecting at least two errors in the operation of at least one of the energy source and the at least one associated device; and prioritizing one of the at least two errors over at least one other of the at least two errors based on at least one characteristic of each of the at least two errors;

whereby detecting at least two errors comprises comparing at least one of input measurements, output measurements, and configuration parameters for the operation of the energy source and the at least one associated device, with respective expected measurements or expected parameters, or both.

2. The method of claim 1, wherein each of the errors is prioritized during the step of prioritizing at least one of the at least two errors.

3. The method of claim 1, wherein the characteristic comprises a factor associated with resolving each of the at least two errors.

4. The method of claim 1, wherein the characteristic comprises a severity of each of the at least two errors.

5. The method of claim 3, wherein the factor associated with resoling each of the at least two errors comprises a complexity of resolving each of the at least two errors.

6. The method of claim 3, wherein the factor associated with resoling each of the at least two errors comprises a degree to which resolving each of the at least two errors will resolve another error.

7. The method of claim 1, whereby at least some of the expected measurements and expected parameters are responsive to manual changing.

8. The method of claim 1, whereby at least some of the expected measurements and expected parameters are responsive to a mode of operation of the energy source.

9. The method of claim 1, whereby at least some of the expected measurements and expected parameters are responsive to measurements input into the system.

10. The method of claim 1, whereby at least some of the expected measurements and expected parameters are responsive to said first or second errors.

11. The method of claim 1, comprising classifying the at lease two errors in response to specific values of the input measurements, output measurements, and configuration parameters used in the detection of said errors.

12. The method of claim 1, wherein the step of prioritizing comprises referencing predetermined criteria for assigning a priority to each of the at least two errors.

13. The method of claim 1, wherein the step of prioritizing is responsive at least in part to an order in which the at east two errors were detected.

14. The method of claim 1, wherein the energy source is a radio-frequency generator.

15. The method of claim 1, further comprising a step of prioritizing a response to the higher priority error relative to a response to any other error.

16. The method of claim 15, wherein an error message responsive to the higher priority error is displayed such that it at least partially obscures an error message responsive to a lower priority error.

17. The method of claim 1, wherein the energy source comprises a plurality of inputs.

18. The method of claim 17, wherein the plurality of inputs is selected from the group consisting of inputs from measuring devices and inputs that relay information on the type and quantity of any devices attached to the energy source.

19. The method of claim 17, wherein at least two errors comprises at least two errors responsive to signals received substantially concurrently from at least two of the plurality of inputs.

20. The method of claim 4, wherein an error that is more complex to resolve is prioritized over an error that is simpler to resolve.

21. A method of prioritizing errors in a medical treatment system comprising an energy source and at least one associated device, the method comprising:

detecting at least two errors in the operation of at east one of the energy source and the at east one associated device;

prioritizing one of the at least two errors over at least one other of the at least two errors based on at least one characteristic of each of the at least two errors; and outputting a display of the at least two errors based on their relative priority;

wherein outputting a display comprises displaying the at least two errors such that the display of the higher priority error at least partially obscures the display of a lower priority error.

22. The method of claim 21, wherein resolving the higher priority error results in the display of the lower priority error becoming unobstructed.

23. A method of prioritizing errors in a medical treatment system comprising an energy source and at least one associated device, the method comprising:

detecting at least two errors in the operation of at least one of the energy source and the at least one associated device; and prioritizing one of the at least two errors over at least one other of the at least two errors based on at least one characteristic of each of the at least two errors;

wherein the one of the at least two errors s related to a first parameter of energy delivery, and wherein the at least one other of the at east two errors is related to a second parameter of energy delivery different than the first parameter of energy delivery, and wherein the one of the errors is prioritized over the at least one other of the at least two errors based on a relative severity of the errors.

* * * * *